United States Patent
Iwasaki et al.

(10) Patent No.: US 6,189,574 B1
(45) Date of Patent: Feb. 20, 2001

(54) FLEXIBLE TUBE FOR ENDOSCOPE

(75) Inventors: Tomoko Iwasaki, Chiba-ken; Kenichi Ohara, Gunma-ken; Akira Sugiyama, Kanagawa-ken; Naoya Ouchi, Saitama-ken, all of (JP)

(73) Assignee: Asahi Kogaku Kogyo Kabushiki Kaisha, Tokyo (JP)

( * ) Notice: Under 35 U.S.C. 154(b), the term of this patent shall be extended for 0 days.

(21) Appl. No.: 09/572,859

(22) Filed: May 18, 2000

(30) Foreign Application Priority Data

May 18, 1999 (JP) .................................................. 11-136884

(51) Int. Cl.$^7$ ...................................................... F16L 55/00
(52) U.S. Cl. ............................ 138/104; 138/177; 138/178; 138/DIG. 11; 116/205
(58) Field of Search ...................................... 138/104, 177, 138/178, DIG. 11; 116/205, DIG. 15

(56) References Cited

U.S. PATENT DOCUMENTS

| | | | |
|---|---|---|---|
| 2,630,033 | * | 3/1953 | Stover ........................................ 81/15 |
| 3,367,370 | * | 2/1968 | Sherlock ................................ 138/104 |
| 3,451,434 | * | 6/1969 | Bauer, Jr. .............................. 138/172 |
| 5,182,954 | * | 2/1993 | Menheere ........................... 138/104 X |
| 5,622,210 | * | 4/1997 | Crisman et al. ...................... 138/104 |

* cited by examiner

*Primary Examiner*—Patrick Brinson
(74) *Attorney, Agent, or Firm*—Greenblum & Bernstein, P.L.C.

(57) ABSTRACT

A flexible tube for an endoscope is provided with a tubular sheath. An outer circumferential surface of the sheath is provided with an indicator that indicates at least one of an orientation of the sheath about an axis thereof and axial length information. The indicator includes at least one striation extending in the axial direction of the sheath. The striation is formed to be perceptible by touch.

10 Claims, 10 Drawing Sheets

FLEXIBLE TUBE FOR ENDOSCOPE

BACKGROUND OF THE INVENTION

The present invention relates to a flexible tube for an endoscope.

Generally, a flexible tube, which is to be inserted in a human cavity, of an endoscope is provided with an observation window at the tip end portion thereof. Further, in order to identify an orientation of the inserted portion and an inserted depth with respect to an entrance (i.e., a mouth, an anus or the like), indication of a distance from the tip of the insertion portion and the orientation is generally provided. In a conventional flexible tube, as the indication, optically recognizable marks are formed, for example, by printing.

When an optical endoscope is used, when an operator is observing through an eyepiece lens, by simply dropping the eyes a little, the operator can recognize the marks on the insertion portion.

However, when an electronic endoscope, which has spread widely, is used, the observation is usually done through a monitor device such as a CRT monitor, which are usually located at an upper level. Accordingly, when the marks are to be checked, the operator is required to move the sight line by a large amount. Such an action is troublesome. Further, the mark may not be found easily in such a case, and in a worse case, the operator may overlook a diseased portion.

SUMMARY OF THE INVENTION

It is therefore an object of the present invention to provide an improved flexible tube for an endoscope with which the operator can recognize indication marks easily without shifting the sight line greatly.

For the above object, according to the present invention, there is provided a flexible tube for an endoscope, having a tubular sheath, an outer circumferential surface of the sheath being provided with an indicator that indicates at least one of an orientation of the sheath about an axis thereof and axial length information, the indicator includes at least one striation extending in the axial direction of the sheath. It should be noted that the striation is formed to be perceptible by touch.

Since an operator can feel the striation, the orientation and/or distance information can be recognized only by touch.

Optionally, at least one striation includes a protrusion extending in the axial direction of the sheath. Alternatively, the striation may be a groove extending in the axial direction of the sheath.

Further optionally, a configuration of the indicator varies along the axis of the sheath.

With this structure, by feeling the indicator, the operator can recognize borders at a position where the configuration changes.

In one case, the configuration may include a cross sectional shape of the at least one striation.

Optionally or alternatively, the configuration may include a continuous/intermittent condition of the at least one striation.

Further optionally or alternatively, the configuration may include a plurality of intermittent conditions of the at least one striation.

Optionally, a visually recognizable indication can be provided on the sheath as well as the indication that is perceptible by touch.

Further more, the indicator may include a first indicator having at least one striation and a second indicator having at least one striation, the first and second indicators being provided at different circumferential positions on the sheath, configurations of the first and second indicators being different from each other.

In one example, the configurations of the first and second indicators are different in terms of the number of striations.

BRIEF DESCRIPTION OF THE ACCOMPANYING DRAWINGS

FIG. 1 schematically shows an appearance of an endoscope to which the invention is applied;

DETAILED DESCRIPTION OF THE EMBODIMENTS

Hereinafter, embodiments of the present invention will be described with reference to the accompanying drawings.

Figure 1:
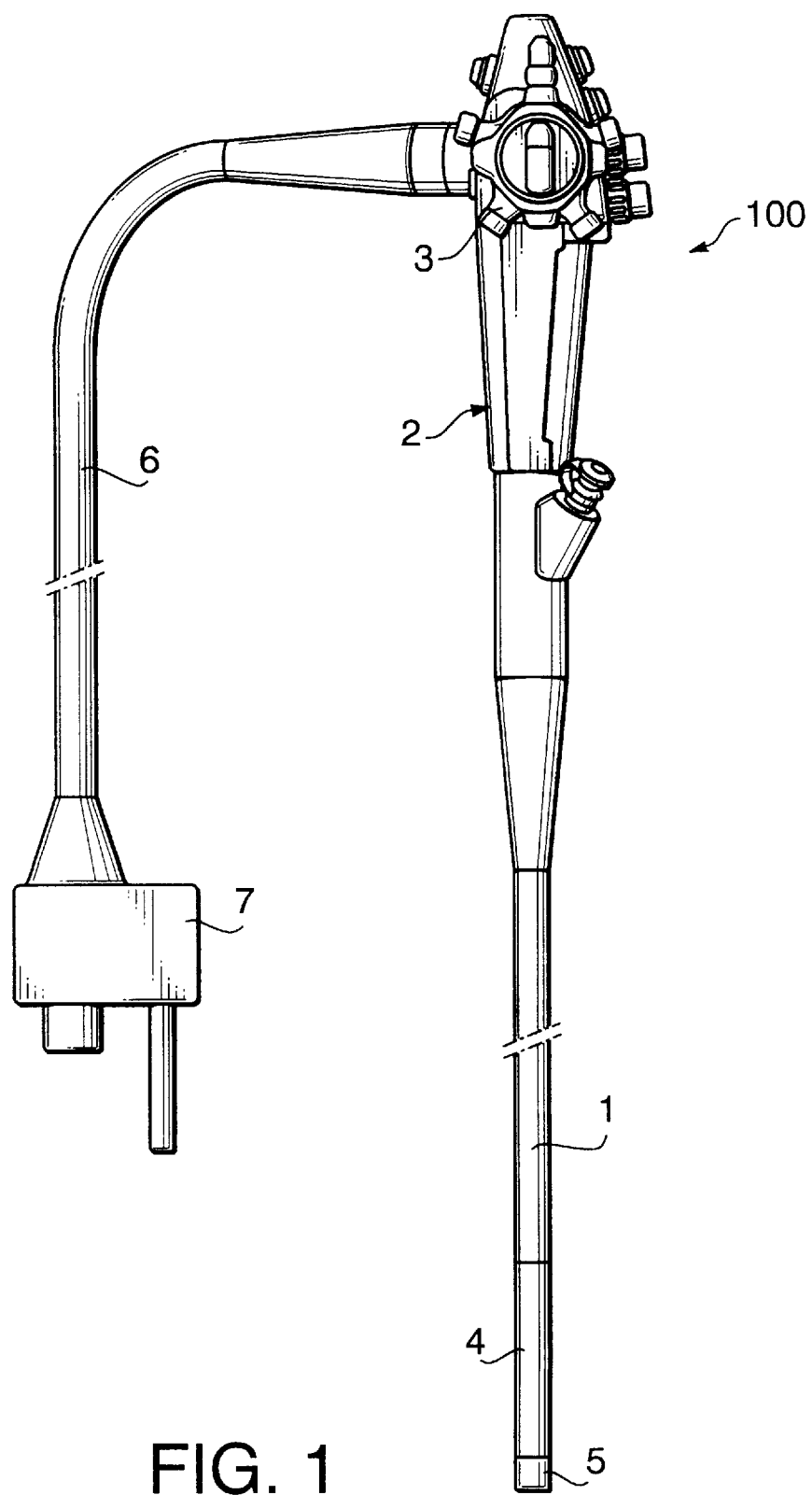

FIG. 1 schematically shows an appearance of an endoscope 100 to which the embodiments of the present invention is applicable.

The endoscope 100 includes a flexible tube 1 which is to be inserted in a human cavity. The proximal end of the flexible tube 1 is connected to the distal end portion (a lower end in FIG. 1) of an operation unit 2.

A tip of the flexible tube 1 is connected to a bendable portion 4, which can be bent at an arbitrary angle in an arbitrary direction with operation of a knob 3 provided to the operation unit 2. To the tip of the bendable portion 4, an main body 5 accommodating an objective optical system is connected.

To the tip of a flexible connecting tube 6 that is connected to an upper end portion of the operation unit 2, a connector 7 is provided. The connector 7 is to be connected to a video processor provided with a built-in light source unit (not shown) for supplying light to illuminate an object via an illuminative optical unit of the main body 5 and for processing image signals obtained through the objective optical system of the main body 5.

Figure 2:
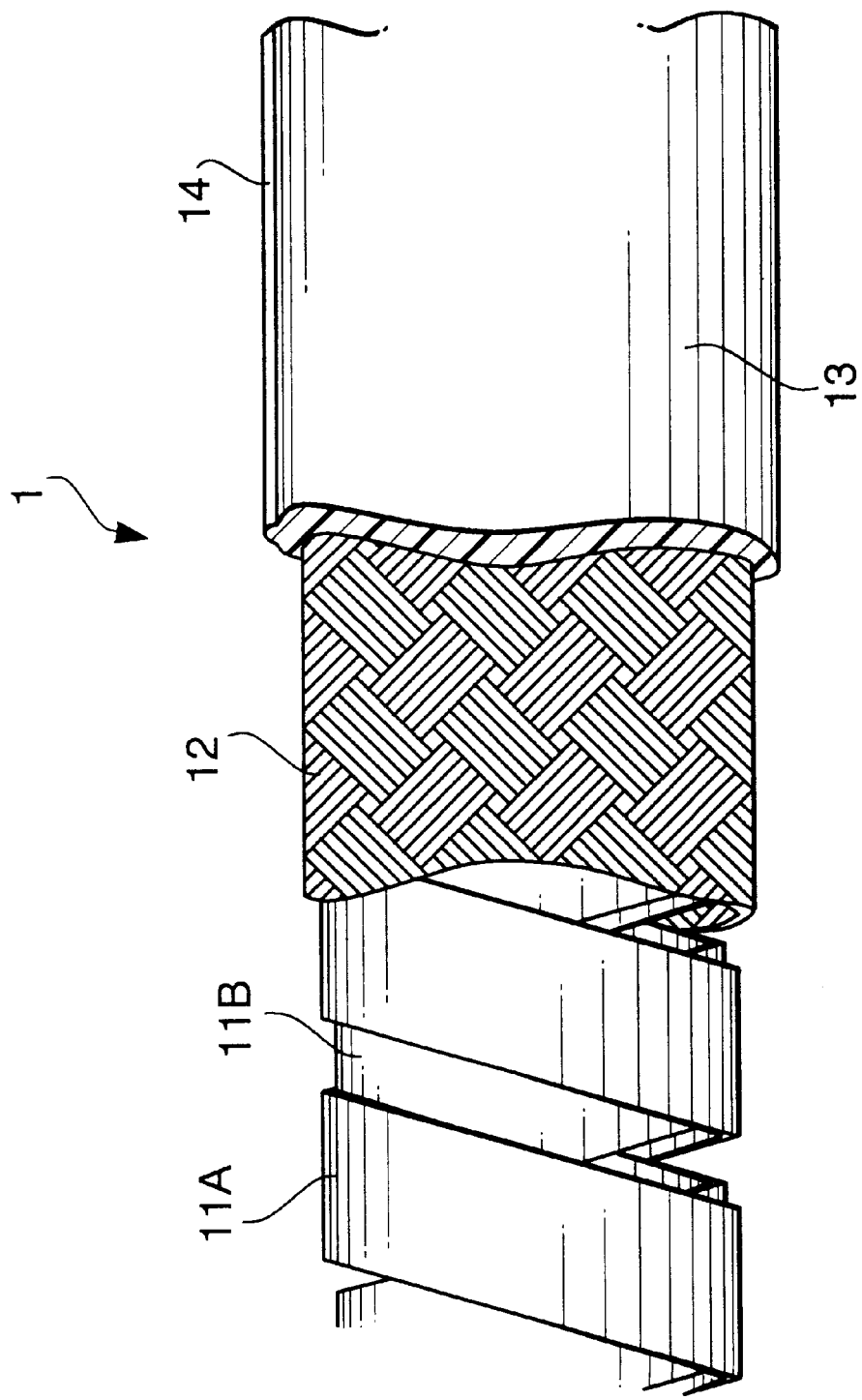
FIG. 2 shows a basic structure of a flexible tube.

FIG. 2 shows a basic structure of the flexible tube 1 according to a first embodiment. The innermost layer of the flexible tube 1 is a spirally-wound tubes 11A and 11B. Each of the spirally-wound tubes 11A and 11B is formed by spirally winding belt-shaped metal such as stainless steel or copper alloy in a pitch (axial) direction of the tube. In this example, two spirally-wound tubes 11A and 11B whose winding directions are opposite are provided. The invention is not limited to the application to an endoscope having such a structure. The invention is applicable to an endoscope provided with a single spirally-wound tube or more than two spirally-wound tubes.

The spirally-wound tubes 11A and 11B are covered with a braided tube 12 which is formed with braided thin metal or non-metal wires. Further, the braided tube 12 is coated with a synthetic resin layer, or a flexible sheath 13 made of a synthetic resin.

The sheath 13 is made of, for example, material having polyurethane as the main ingredient. A pellet of the material is put in an extrusion molding device, and heat-melted material is directly applied onto the outer surface of the braided tube 12, and then cooled, so that a tubular sheath 13 is formed on the braided tube 12. It should be noted that the sheath 13 is not necessarily be formed in accordance with the extrusion molding method. Further, on the sheath 13, a protruded striation 14 is formed along the axis of the sheath 13. The circumferential position on the sheath 13 where the protruded striation 14 is formed corresponds to the upper portion of an observed field.

Figure 3:
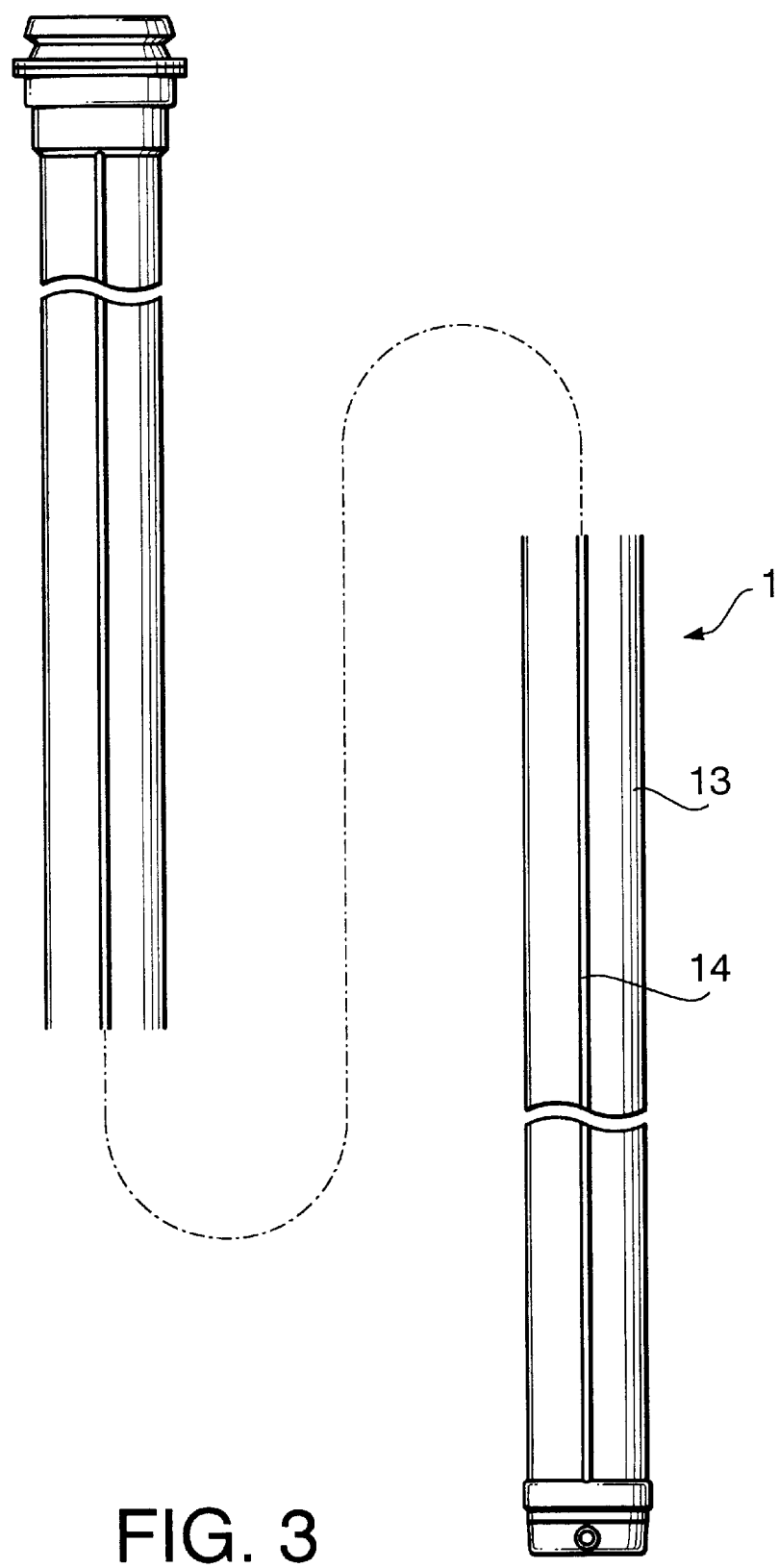
FIG. 3 is a side view of a flexible tube according to a first embodiment.
Figure 4:
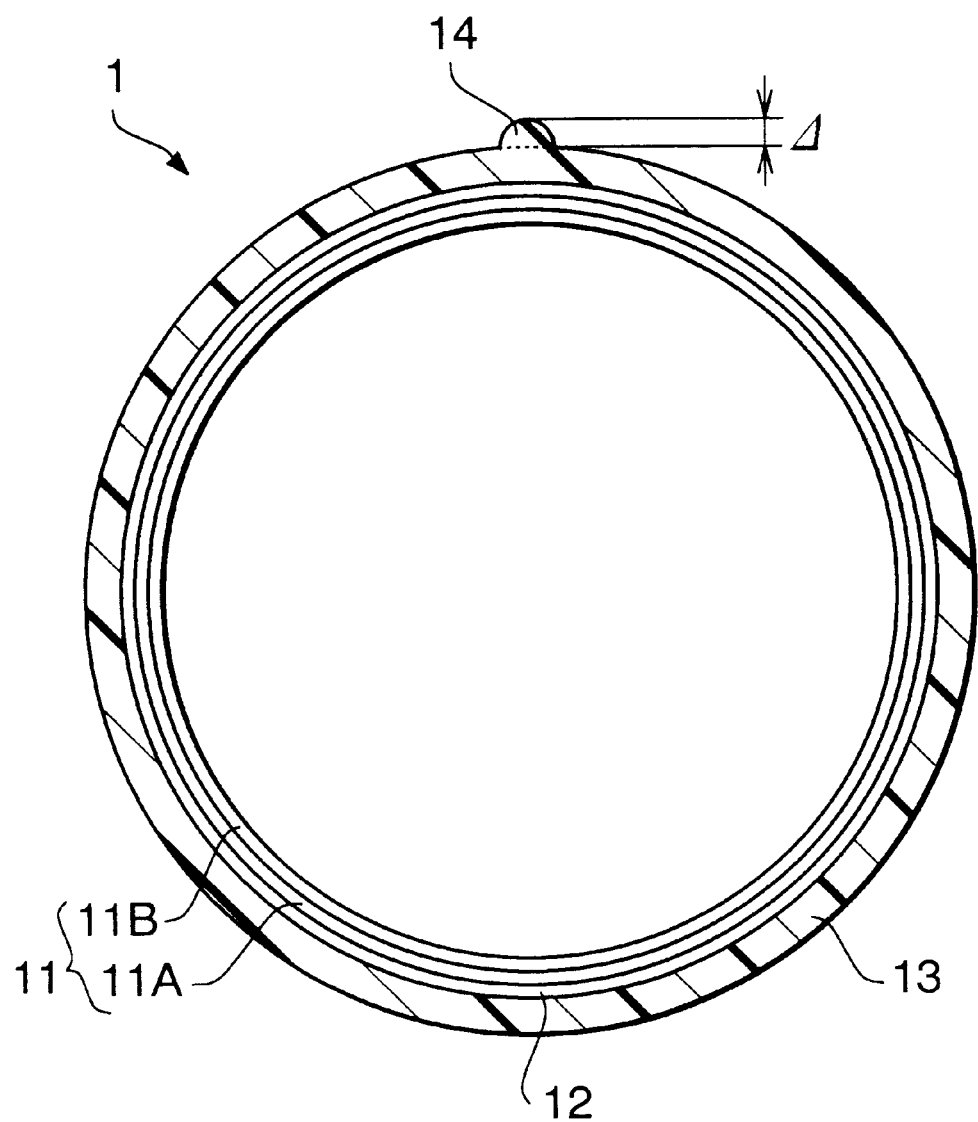
FIG. 4 is a cross sectional view of the flexible tube, taken along a plane perpendicular to an axis thereof, according to the first embodiment of the invention.

FIG. 3 is a side view of the flexible tube 1, according to a first embodiment of the invention. FIG. 4 is a cross sectional view of the flexible tube 1, taken along a plane perpendicular to the axis thereof, according to the first embodiment. In this embodiment, the striation 14 extends continuously over an entire length of the sheath 13. The striation 14 is formed to be perceptible by touch. That is, the striation 14 is protruded from the circumferential surface of the sheath 13 by a barely enough amount the operator can feel with his/her fingers (see FIG. 4). As shown in FIG. 4, the cross section of the striation 14 is semicircular, and a protruded amount Δ is, for example, 0.01 mm–0.5 mm.

The striation 14 as described above may be formed easily by adjusting a shape of a die of the extrusion molding device. The striation 14 does not indicate length information. However, in regard with the orientation about the axis of the flexible tube 1, the operator can recognize it only by feeling the striation 14, without viewing the same.

Figure 5:
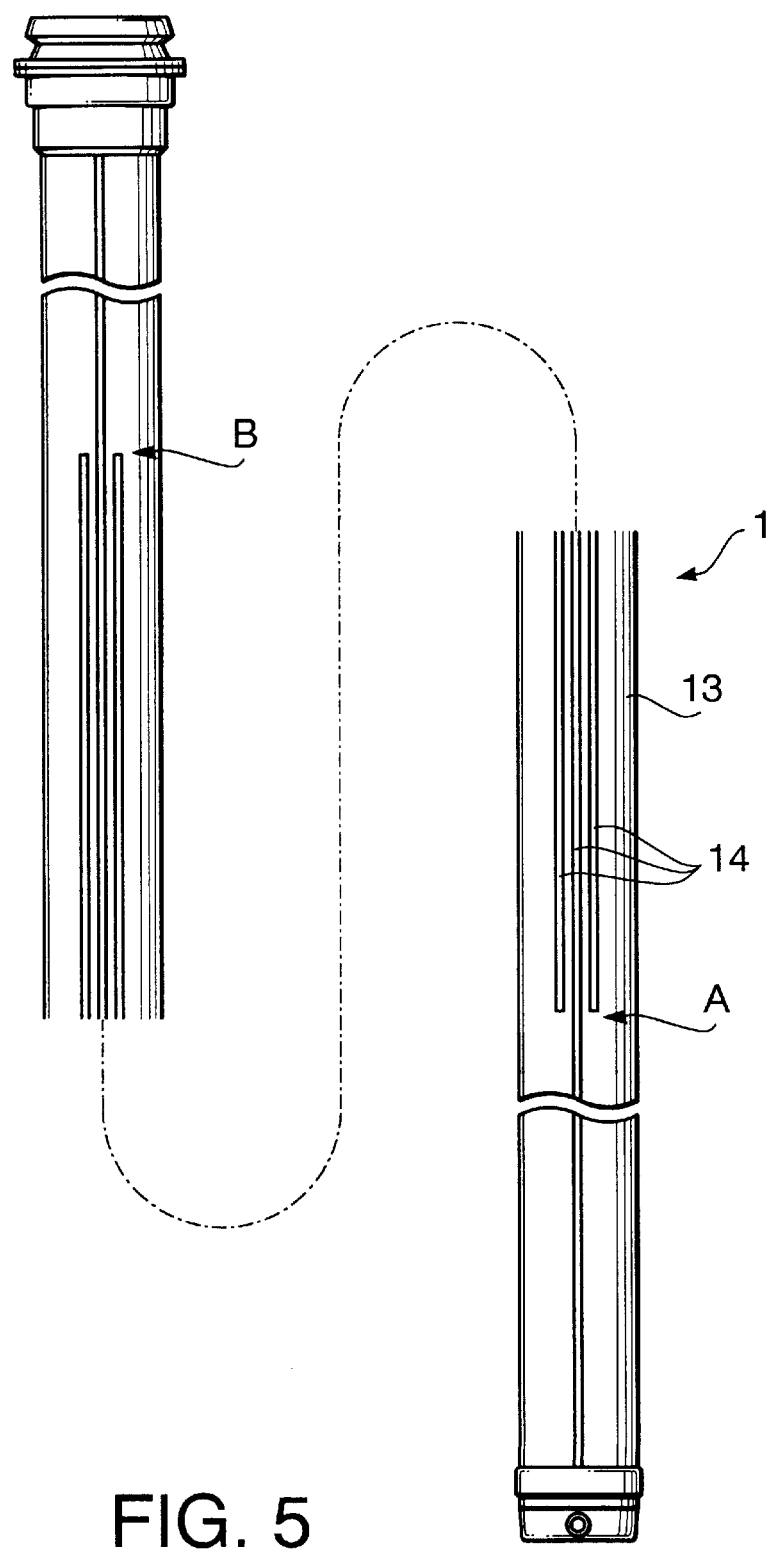
FIG. 5 is a side view of a flexible tube according to a second embodiment.

FIG. 5 is a side view of a flexible tube according to a second embodiment.

In the second embodiment, the number of the striations 14 is changed depending on the axial position of the sheath 13. Specifically, in FIG. 5, at the axial end side portions of the sheath 13, a single striation is formed, while at the intermediate portion, three striations are formed. Borders A and B, at which the number of the striations 14 is changed, are determined to be apart from the main body 5 by predetermined distances, respectively. It should be noted that the cross sectional shape of the striations 14 is similar to that of the first embodiment.

According to the second embodiment, the operator can recognize the orientation about the axis of the flexible tube based on the circumferential position of the striations 14, and further, by feeling the borders A and B, the operator can also recognize the distance information (i.e., an insertion depth).

It should be noted that it is also possible to form an axial area, on the sheath 13, where two striations 14 are formed. In this case, the borders can be defined between the axial areas where a single striation, two striations and three striations are formed. Further, it should be noted that the maximum number of the striations 14 could be more than three.

Figure 6:
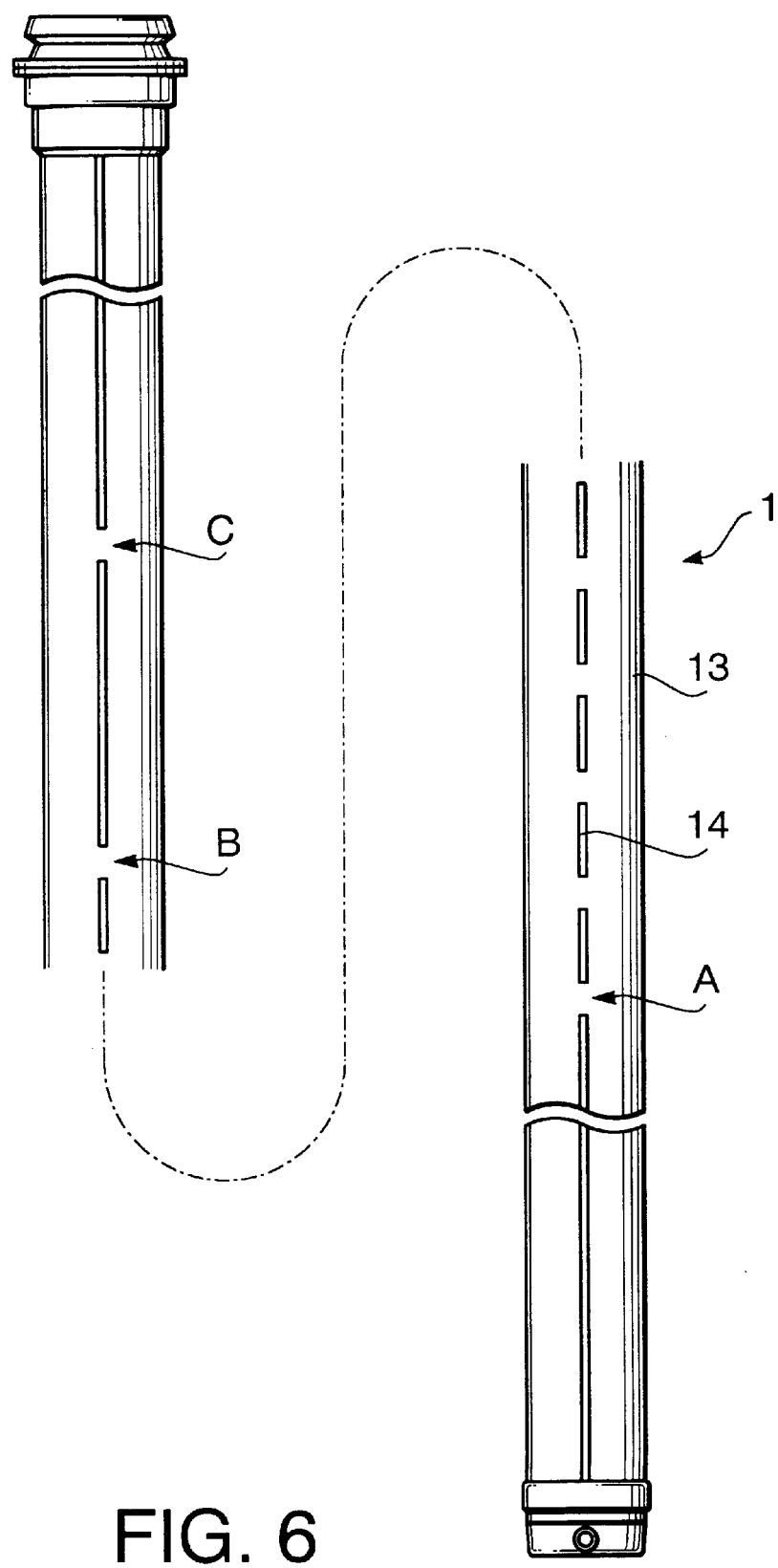
FIG. 6 is a side view of a flexible tube according to a third embodiment.

FIG. 6 is a side view of a flexible tube according to a third embodiment.

In the third embodiment, the striation 14 is formed intermittently (like a broken line). In the example shown in FIG. 6, the striation 14 is formed continuously at the axial end portions of the sheath 13, while at the intermediate portion, the striation 14 is formed intermittently. Thus, borders A and C are defined at which the intermittent/continuous condition is changed. Further, at a midst of the intermittent area (between the borders A and C), the intermittent condition is changed at a border B. The borders A, B and C are located at predetermined positions with respect to the main body 5 of the endoscope 100. It should be noted that the cross sectional shape of the striations 14 is similar to that of the first embodiment.

According to the third embodiment, the operator can recognize the orientation about the axis of the flexible tube based on the circumferential position of the striation 14, and further, by feeling the borders A, B and C, the operator can also recognize the distance information (i.e., an insertion depth) or currently located area (i.e., an area between the borders A and B or an area between the borders B and C).

It should be noted that, by changing the intermittent/continuous conditions, the number of borders can be increased arbitrarily.

Figure 7:
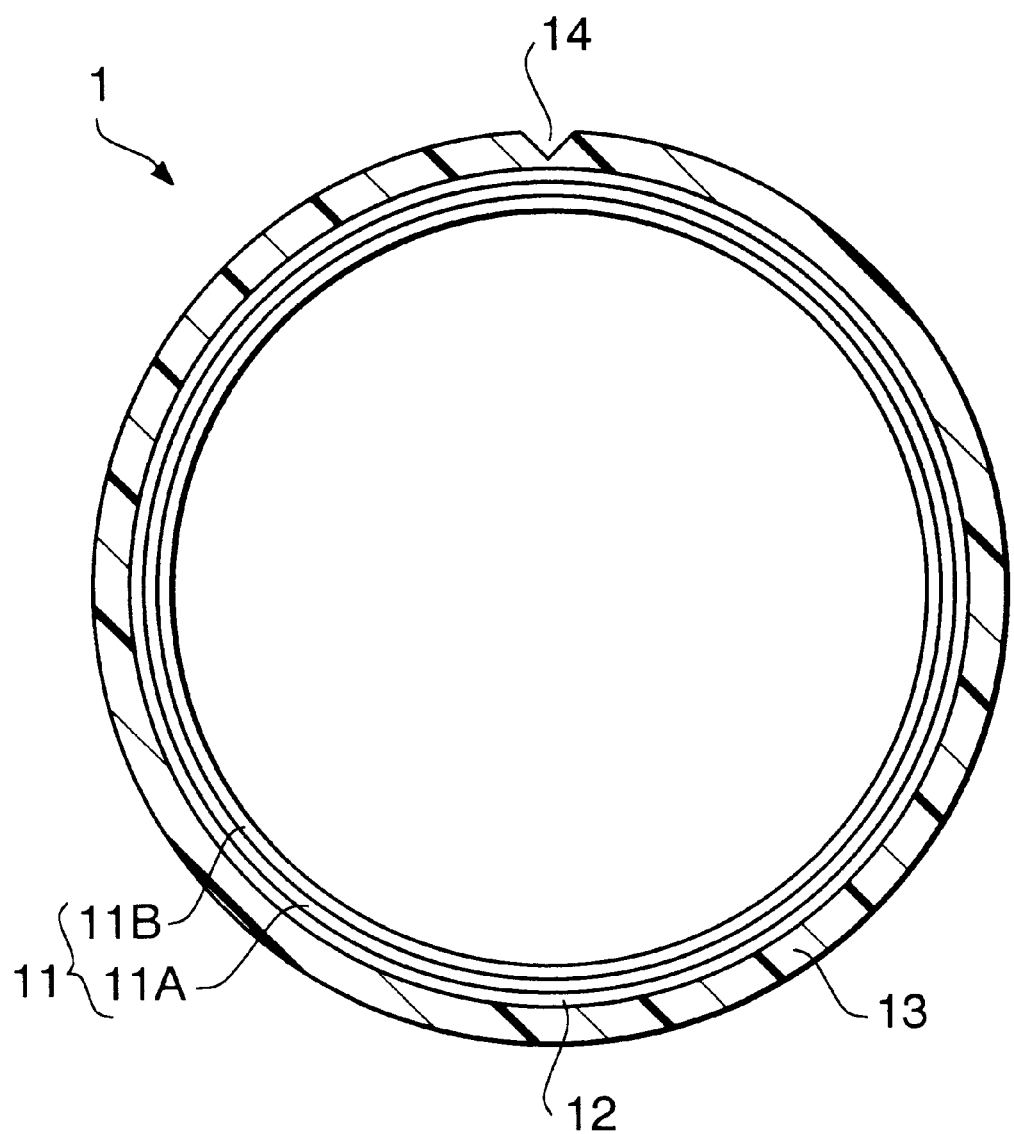
FIG. 7 is a cross sectional view of the flexible tube, taken along a plane perpendicular to an axis thereof, according to a fourth embodiment of the invention.

FIG. 7 is a cross sectional view of the flexible tube 1, taken along a plane perpendicular to an axis thereof, according to a fourth embodiment of the invention.

The fourth embodiment is similar to the first or third embodiment except that the striation 14 formed as a groove but not a protrusion. As shown in FIG. 7, the cross section of the striation 14 is V-shaped.

It should be noted that the cross section of the striation 14 is not limited to the V-shaped. It may be formed to be U-shaped, or any other appropriate shape.

It should be noted that it may be possible to form a striation 14 to have a protrusion or groove depending on the axial position of the sheath 13. In such a case, even if the striation 14 is continuous as in the first embodiment, borders can be defined, similarly to the second embodiment, along the axis of the sheath 13, and the distance information can also be indicated by the striation 14.

Figure 8:
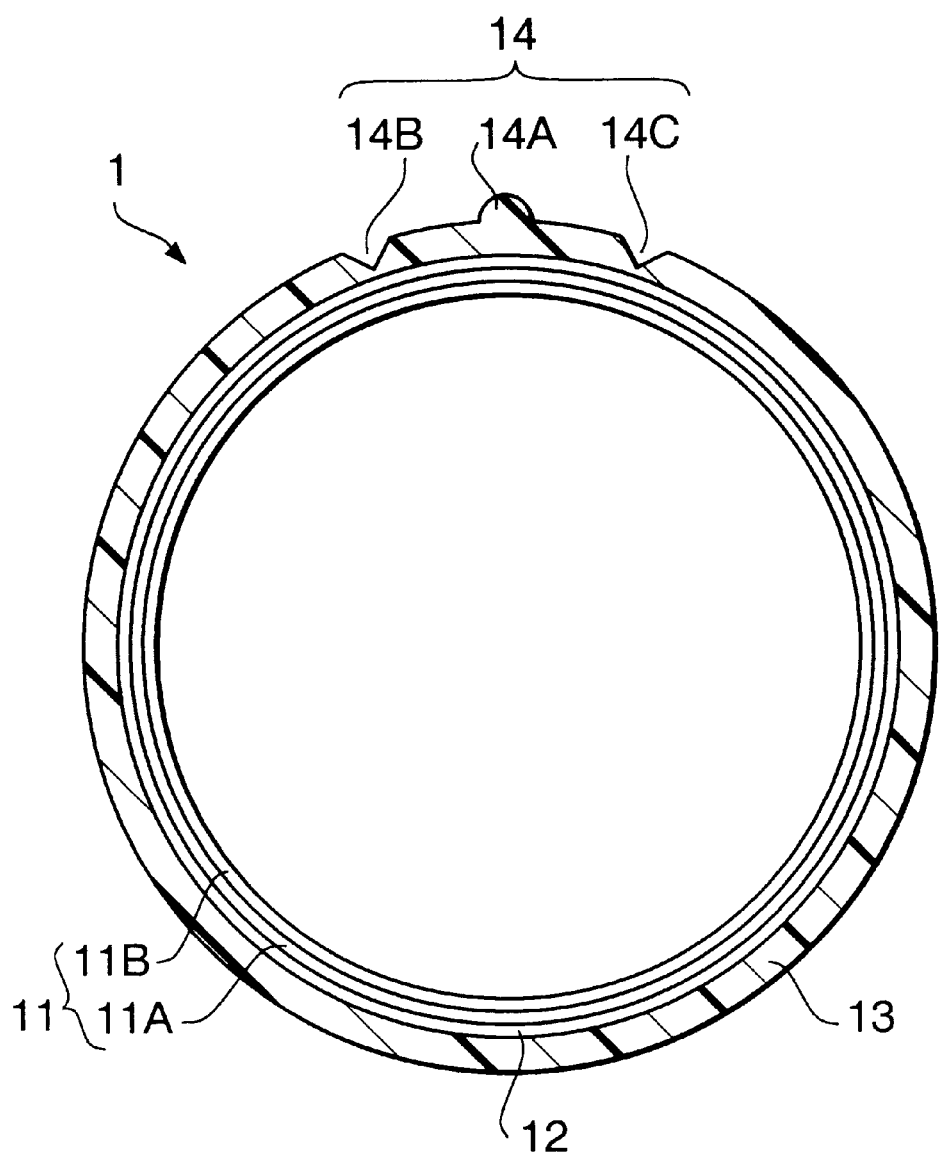
FIG. 8 is a cross sectional view of the flexible tube, taken along a plane perpendicular to an axis thereof, according to a fifth embodiment of the invention.

FIG. 8 is a cross sectional view of the flexible tube 1, taken along a plane perpendicular to an axis thereof, according to a fifth embodiment of the invention.

The fifth embodiment is similar to the second embodiment except that the striations 14 include a protrusion 14A and grooves 14B and 14C. As shown in FIG. 8, the cross section of the striations 14B and 14C is V-shaped.

It should be noted that the cross section of the striation 14B and 14C is not limited to the V-shaped. It may be formed to be U-shaped, or any other appropriate shape.

Further, each of the striations 14A–14C can be formed either a protrusion or a groove. A combination of protrusions and grooves for the striations 14 may be changed depending on the axial position of the sheath 14. In such a case, the combinations define borders, which represent distance information.

Figure 9:
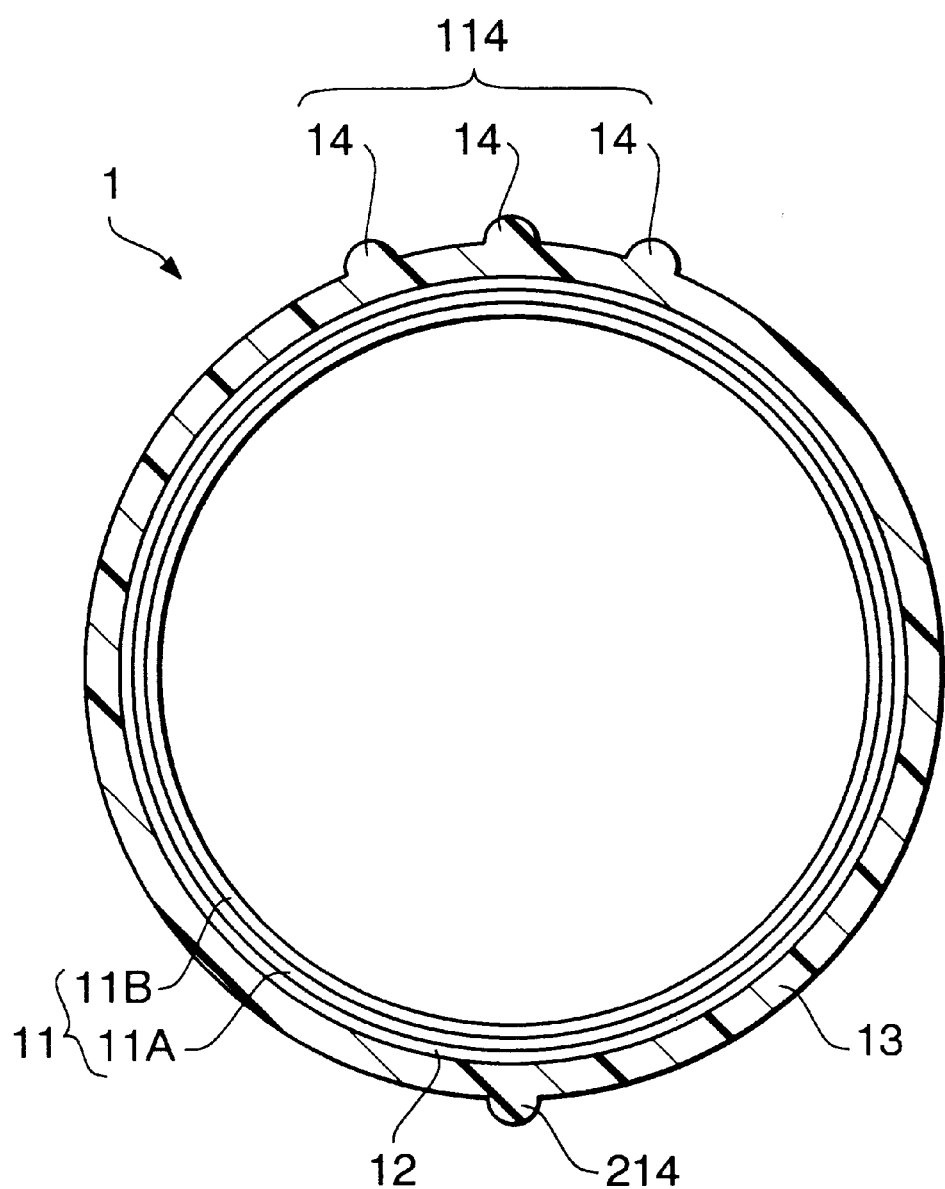
FIG. 9 is a cross sectional view of the flexible tube, taken along a plane perpendicular to an axis thereof, according to a sixth embodiment of the invention.

FIG. 9 is a cross sectional view of the flexible tube 1, taken along a plane perpendicular to an axis thereof, according to a sixth embodiment of the invention.

In the sixth embodiment, On one circumferential position on the sheath 13, striation(s) 114 having a first configuration (i.e., a plurality of striations 14) are provided, and on the opposite portion, a striation 214 having a second configuration (i.e., a single striation 14) is provided.

With this structure, the operator can feel the orientation about the axis of the sheath 13 with two distinct striations 114 and 214.

It should be noted that the first and second configurations are not limited to those shown in FIG. 9. For example, the first configuration could be a single protruded striation 14 and the second configuration could be a single groove. Various combination can be employed for the first and second configurations.

Further, more than two configurations may be employed and striations may be provided more than two circumferential positions on the sheath 13.

Figure 10:
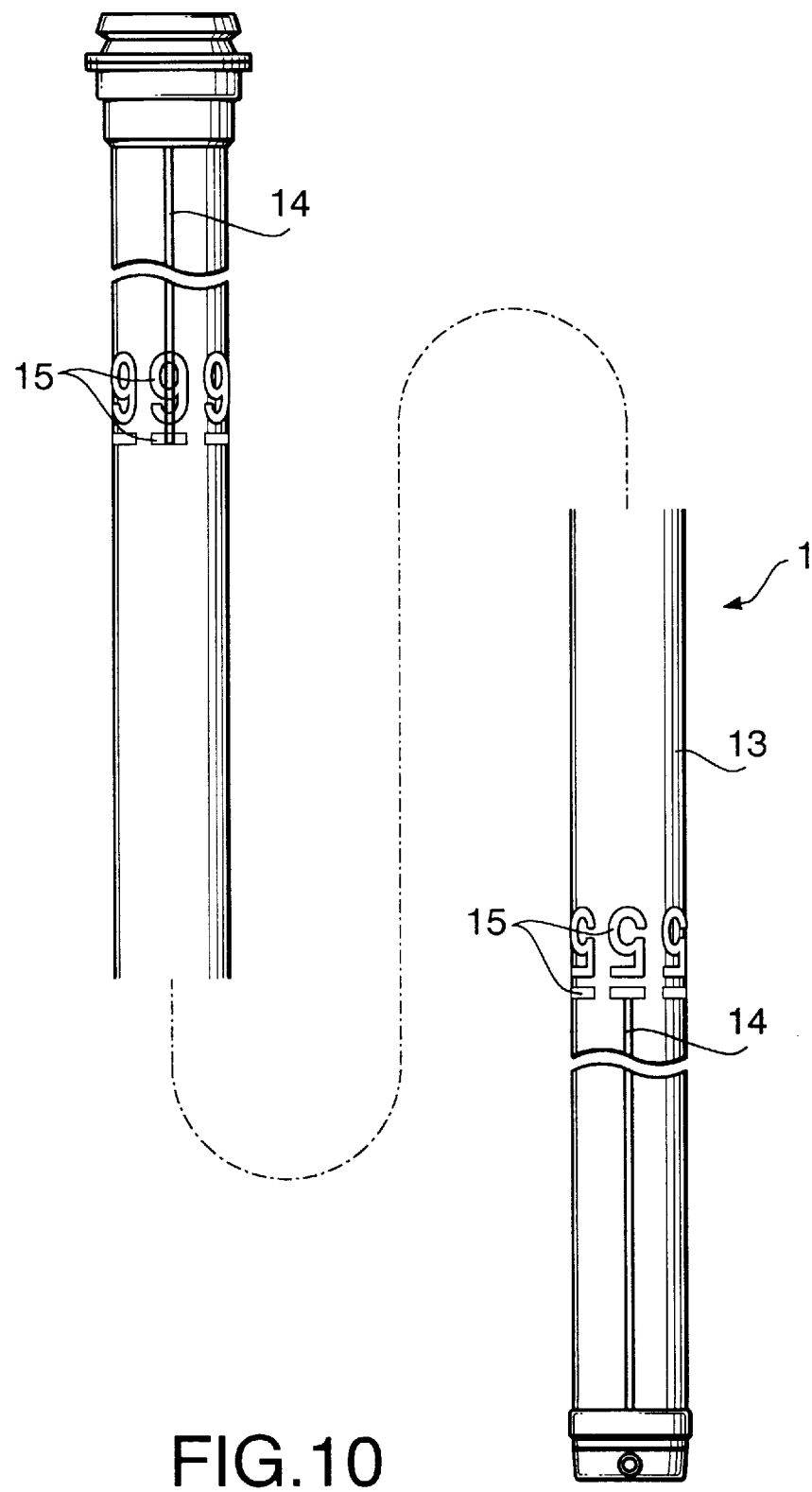
FIG. 10 is a side view of a flexible tube according to a seventh embodiment.

FIG. 10 is a side view of a flexible tube 1 according to a seventh embodiment.

In the seventh embodiment, the striation 14 as in the first embodiment and visible indications 15 are formed on the circumferential surface of the flexible tube 1.

With this structure, the operator can recognize the orientation and/or distance information through eyes as well as by feeling the striation 14.

It should be noted that the striation 14 is not limited to the one shown in FIG. 10. Any type of striation(s) 14 can be used in the seventh embodiment.

Further, any suitable combination of the striations of first through seventh embodiments can also enable the operator to recognize the orientation and distance information easily.

The present disclosure relates to the subject matter contained in Japanese Patent Application No. HEI 11-136884, filed on May 18, 1999, which is expressly incorporated herein by reference in its entirety.

What is claimed is:

1. A flexible tube for an endoscope, having a tubular sheath, an outer circumferential surface of said sheath being provided with an indicator that indicates at least one of an orientation of said sheath about an axis thereof and axial length information, said indicator includes at least one striation extending in the axial direction of said sheath, said at least one striation being perceptible by touch.

2. The flexible tube according to claim 1, wherein said at least one striation includes a protrusion extending in the axial direction of said sheath.

3. The flexible tube according to claim 1, wherein said at least one striation includes a groove extending in the axial direction of said sheath.

4. The flexible tube according to claim 1, wherein a configuration of said indicator varies along the axis of said sheath.

5. The flexible tube according to claim 4, wherein said configuration includes a cross sectional shape of said at least one striation.

6. The flexible tube according to claim 4, wherein said configuration includes a continuous/intermittent condition of said at least one striation.

7. The flexible tube according to claim 4, wherein said configuration includes a plurality of intermittent conditions of said at least one striation.

8. The flexible tube according to claim 1, wherein a visually recognizable indication is provided on said sheath.

9. The flexible tube according to claim 1, wherein said indicator includes a first indicator having at least one striation and a second indicator having at least one striation, said first and second indicators being provided at different circumferential positions on said sheath, configurations of said first and second indicators being different from each other.

10. The flexible tube according to claim 9, wherein the configurations of said first and second indicators are different in terms of the number of striations.

* * * * *